US008728536B2

(12) United States Patent
Lee et al.

(10) Patent No.: US 8,728,536 B2
(45) Date of Patent: **\*May 20, 2014**

(54) CHEMOTHERAPEUTIC COMPOSITION USING NANOCRYSTALLINE CALCIUM PHOSPHATE PASTE

(75) Inventors: Dosuk D Lee, Brookline, MA (US); Maria Aiolova, Brookline, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/397,029

(22) Filed: Mar. 30, 2006

(65) Prior Publication Data

US 2006/0240121 A1    Oct. 26, 2006

Related U.S. Application Data

(63) Continuation of application No. 09/693,120, filed on Oct. 20, 2000, now abandoned, which is a continuation of application No. 09/153,133, filed on Sep. 15, 1998, which is a continuation of application No. 08/729,342, filed on Oct. 16, 1996, now Pat. No. 6,541,037.

(51) Int. Cl.
*A61K 33/42* (2006.01)
*A61K 38/00* (2006.01)

(52) U.S. Cl.
USPC .......................... 424/602; 423/308; 423/311

(58) Field of Classification Search
USPC .................................. 424/602; 423/308, 311
See application file for complete search history.

(56) References Cited

U.S. PATENT DOCUMENTS

| | | | |
|---|---|---|---|
| 2,967,802 A | 1/1961 | Towey et al. | 424/244.1 |
| 3,608,071 A | 9/1971 | Relyveld et al. | 424/217.1 |
| 3,925,545 A | 12/1975 | Relyveld | 424/238.1 |
| 4,016,252 A | 4/1977 | Relyveld | 424/212.1 |
| 4,108,690 A | 8/1978 | Heller | 148/263 |
| 4,110,432 A | 8/1978 | Wilkinson et al. | 424/158.4 |
| 4,157,378 A | 6/1979 | Tomlinson et al. | 423/301 |
| 4,302,446 A * | 11/1981 | Kaplan et al. | 424/649 |
| 4,329,332 A | 5/1982 | Couvreur et al. | 424/9.6 |
| 4,346,709 A | 8/1982 | Schmitt | 424/426 |
| 4,347,234 A | 8/1982 | Wahlig et al. | 424/426 |
| 4,353,888 A | 10/1982 | Sefton | 424/424 |
| 4,429,691 A | 2/1984 | Niwa et al. | 606/77 |
| 4,609,551 A | 9/1986 | Caplan et al. | 424/549 |
| 4,612,053 A | 9/1986 | Brown et al. | 106/35 |
| 4,620,327 A | 11/1986 | Caplan et al. | 623/10 |
| 4,684,673 A | 8/1987 | Adachi | 523/116 |
| 4,737,411 A | 4/1988 | Graves, Jr. et al. | 428/403 |
| 4,842,603 A | 6/1989 | Draenert | 623/23.56 |
| 4,849,193 A | 7/1989 | Palmer et al. | 423/308 |
| 4,880,610 A | 11/1989 | Constantz | 423/309 |
| 4,892,538 A | 1/1990 | Aebischer et al. | 604/891.1 |
| RE33,161 E | 2/1990 | Brown et al. | 249/148 |
| 4,917,702 A | 4/1990 | Scheicher et al. | 424/423 |
| RE33,221 E | 5/1990 | Brown et al. | 510/130 |
| 4,938,938 A | 7/1990 | Ewers et al. | 423/308 |
| 4,959,104 A | 9/1990 | Iino et al. | 106/691 |
| 5,007,930 A | 4/1991 | Dorman et al. | 427/2.27 |
| 5,034,059 A | 7/1991 | Constantz | 106/151.1 |
| 5,037,639 A | 8/1991 | Tung | 424/57 |
| 5,041,138 A | 8/1991 | Vacanti et al. | 424/422 |
| 5,047,031 A | 9/1991 | Constantz | 606/77 |
| 5,053,212 A | 10/1991 | Constantz et al. | 423/305 |
| 5,085,861 A | 2/1992 | Gerhart et al. | 424/78.17 |
| 5,129,905 A | 7/1992 | Constantz | 606/76 |
| 5,149,368 A | 9/1992 | Liu et al. | 424/602 |
| 5,152,836 A | 10/1992 | Hirano et al. | 106/690 |
| 5,164,187 A | 11/1992 | Constantz et al. | 424/423 |
| 5,178,845 A | 1/1993 | Constantz et al. | 423/305 |
| 5,188,670 A | 2/1993 | Constantz | 188/667 |
| 5,197,985 A | 3/1993 | Caplan et al. | 128/898 |
| 5,226,914 A | 7/1993 | Caplan et al. | 435/325 |
| 5,231,169 A | 7/1993 | Constantz et al. | 530/356 |
| 5,258,044 A | 11/1993 | Lee | 623/66.1 |
| 5,262,166 A | 11/1993 | Liu et al. | 424/423 |
| 5,279,831 A | 1/1994 | Constantz et al. | 424/423 |
| 5,281,265 A | 1/1994 | Liu | 106/35 |
| 5,286,763 A | 2/1994 | Gerhart et al. | 514/772.4 |
| 5,306,305 A | 4/1994 | Lee | 435/325 |
| 5,336,264 A | 8/1994 | Constanz et al. | 424/423 |
| 5,342,441 A | 8/1994 | Mandai et al. | 106/35 |

(Continued)

FOREIGN PATENT DOCUMENTS

| | | |
|---|---|---|
| EP | 0 268 463 | 5/1988 |
| EP | 0 347 028 | 12/1989 |

(Continued)

OTHER PUBLICATIONS

Aoki, "Science and Medical Applications of Hydroxyapatite," *JAAS* 11-15 (1991).
Aggerbeck and Heron, "Adjuvanticity of Aluminum Hydroxide and Calcium Phosphate in Diphtheria-Tetanus Vaccines," *Vaccine* 13:1360-1365 (1995). Abstract only.
Appel et al., "Recent Advances in Implants for Bone Growth Promotion," *Exp. Opin. Ther. Patents* 4:1461 (1994).
Atala et al., "Injectable Alginate Seeded with Chondrocytes as Potential Treatment for Vesicoureteral Reflux," *J. Urol.* 150:745-747 (1993).
Athanasou et al., "Cellular Biology of Bone-Resorbing Cells," *J. Bone Joint Surg. Am.* 78:1096-1112 (1996).

(Continued)

*Primary Examiner* — Renee Claytor
(74) *Attorney, Agent, or Firm* — Clark & Elbing LLP; Todd Armstrong

(57) ABSTRACT

A method and composition are provided for treating cancer in a mammal. The method includes administering to a tumor site of the mammal an anticancer composition comprising a mixture of an anticancer agent and a nanocrystalline or poorly crystalline calcium phosphate paste, said paste comprised of one or more calcium phosphates and a physiologically acceptable fluid, the paste having an injectable or formable consistency at the time of administration and hardenable at the tumor.

12 Claims, 4 Drawing Sheets

(56) References Cited

U.S. PATENT DOCUMENTS

| | | | |
|---|---|---|---|
| 5,352,715 A | 10/1994 | Wallace et al. | 523/115 |
| 5,399,665 A | 3/1995 | Barrera et al. | 528/354 |
| 5,443,832 A | 8/1995 | Amerongen et al. | 424/278.1 |
| 5,455,231 A | 10/1995 | Constantz et al. | 514/21 |
| 5,462,751 A | 10/1995 | Kossovsky et al. | 424/494 |
| 5,470,803 A | 11/1995 | Bonfield et al. | 501/1 |
| 5,486,359 A | 1/1996 | Caplan et al. | 424/93.7 |
| 5,496,399 A | 3/1996 | Ison et al. | 106/35 |
| 5,508,342 A | 4/1996 | Antonucci et al. | 524/788 |
| 5,514,378 A | 5/1996 | Mikos et al. | 424/425 |
| 5,516,532 A | 5/1996 | Atala et al. | 424/548 |
| 5,522,893 A | 6/1996 | Chow et al. | 423/305 |
| 5,525,148 A | 6/1996 | Chow et al. | 106/35 |
| 5,542,973 A | 8/1996 | Chow et al. | 406/35 |
| 5,543,019 A | 8/1996 | Lee et al. | 204/192.15 |
| 5,545,254 A | 8/1996 | Chow et al. | 106/35 |
| 5,565,502 A | 10/1996 | Glimcher et al. | 523/115 |
| 5,569,442 A | 10/1996 | Fulmer et al. | 423/311 |
| 5,571,493 A | 11/1996 | Fulmer et al. | 423/308 |
| 5,580,623 A | 12/1996 | Fulmer et al. | 428/34.1 |
| 5,605,713 A | 2/1997 | Boltong | 427/2.1 |
| 5,650,108 A * | 7/1997 | Nies et al. | 264/122 |
| 5,650,176 A | 7/1997 | Lee et al. | 424/602 |
| 5,665,120 A | 9/1997 | Ohtsuka et al. | 424/423 |
| 5,676,976 A | 10/1997 | Lee et al. | 424/602 |
| 5,683,461 A | 11/1997 | Lee et al. | 424/423 |
| 5,683,496 A | 11/1997 | Ison et al. | 106/35 |
| 5,683,667 A | 11/1997 | Fulmer et al. | 423/311 |
| 5,691,397 A | 11/1997 | Glimcher et al. | 523/115 |
| 5,697,981 A | 12/1997 | Ison et al. | 606/63 |
| 5,700,289 A | 12/1997 | Breitbart et al. | 424/423 |
| 5,702,717 A | 12/1997 | Cha et al. | 424/425 |
| 5,709,742 A | 1/1998 | Fulmer et al. | 106/690 |
| 5,763,092 A | 6/1998 | Lee et al. | 428/469 |
| 5,782,971 A | 7/1998 | Constantz | 106/690 |
| 5,783,217 A | 7/1998 | Lee et al. | 424/602 |
| 5,795,330 A | 8/1998 | Tofighi et al. | 604/82 |
| 5,843,289 A | 12/1998 | Lee et al. | 204/192.3 |
| 5,846,312 A | 12/1998 | Ison et al. | 106/690 |
| 5,885,840 A | 3/1999 | Kamentsky et al. | 423/311 |
| 5,900,254 A | 5/1999 | Constantz | 424/602 |
| 5,904,716 A | 5/1999 | Gendler | 424/423 |
| 5,952,010 A | 9/1999 | Constantz | 424/602 |
| 5,958,904 A | 9/1999 | Cordi et al. | 427/2.24 |
| 5,962,028 A | 10/1999 | Constantz | 424/602 |
| 5,964,932 A | 10/1999 | Ison et al. | 106/35 |
| 5,968,253 A | 10/1999 | Poser et al. | 106/691 |
| 5,980,482 A | 11/1999 | Tofighi et al. | 604/82 |
| 6,002,065 A | 12/1999 | Constantz et al. | 423/308 |
| 6,005,162 A | 12/1999 | Constantz | 128/898 |
| 6,027,742 A | 2/2000 | Lee et al. | 424/422 |
| 6,033,582 A | 3/2000 | Lee et al. | 216/37 |
| 6,053,970 A | 4/2000 | Ison et al. | 106/35 |
| 6,083,229 A | 7/2000 | Constantz et al. | 606/92 |
| 6,117,456 A | 9/2000 | Lee et al. | 424/602 |
| 6,132,463 A | 10/2000 | Lee et al. | 600/36 |
| 6,139,578 A | 10/2000 | Lee et al. | 623/16.11 |
| 6,149,655 A | 11/2000 | Constantz et al. | 606/94 |
| 6,214,368 B1 | 4/2001 | Lee et al. | 424/423 |
| 6,277,151 B1 | 8/2001 | Lee et al. | 623/23.61 |
| 6,287,341 B1 * | 9/2001 | Lee et al. | 623/16.11 |
| 6,331,312 B1 | 12/2001 | Lee et al. | 424/426 |
| 6,334,891 B1 | 1/2002 | Constantz et al. | 106/35 |
| 6,464,889 B1 | 10/2002 | Lee et al. | 216/37 |
| 6,541,037 B1 | 4/2003 | Lee et al. | 424/602 |
| 6,544,290 B1 | 4/2003 | Lee et al. | 623/23.63 |
| 6,582,470 B1 | 6/2003 | Lee et al. | 623/23.55 |
| 6,599,516 B1 | 7/2003 | Knaack | 424/423 |
| 6,840,961 B2 | 1/2005 | Tofighi et al. | 623/23.61 |
| 6,953,594 B2 | 10/2005 | Lee et al. | 424/602 |
| 6,972,130 B1 | 12/2005 | Lee et al. | 424/426 |
| 7,150,879 B1 * | 12/2006 | Lee et al. | 424/422 |
| 2002/0155137 A1 | 10/2002 | Lee et al. | |
| 2002/0155167 A1 | 10/2002 | Lee et al. | |
| 2003/0120351 A1 | 6/2003 | Tofighi et al. | |
| 2004/0097612 A1 | 5/2004 | Rosenberg et al. | |
| 2005/0147551 A1 | 7/2005 | Tofighi et al. | |

FOREIGN PATENT DOCUMENTS

| | | |
|---|---|---|
| EP | 0 664 133 | 7/1995 |
| JP | 63111875 | 5/1988 |
| JP | 63170205 | 7/1988 |
| JP | 2182261 | 7/1990 |
| JP | 5305134 | 11/1993 |
| JP | 6228011 | 8/1994 |
| JP | 7277712 | 10/1995 |
| WO | WO 92/00109 | 1/1992 |
| WO | WO 92/02453 | 2/1992 |
| WO | WO 94/02412 | 2/1994 |
| WO | WO 94/04657 | 3/1994 |
| WO | WO 94/08458 | 4/1994 |
| WO | WO 94/20064 | 9/1994 |
| WO | WO 95/08319 | 9/1994 |
| WO | WO 94/25080 | 11/1994 |
| WO | WO 96/03160 | 2/1996 |
| WO | WO 96/36562 | 11/1996 |
| WO | WO 97/17285 | 5/1997 |
| WO | WO 98/16209 | 4/1998 |

OTHER PUBLICATIONS

Attawia et al., "Immunofluorescence and Confocal Laser Scanning Microscopy Studies of Osteoblast Growth and Phenotypic Expression in Three-Dimensional Degradable Synthetic Matrices," *J. Biomed. Mater. Res.* 29:843-848 (1995).

Attawia et al., "Osteoblast-Like Cell Adherence and Migration Through 3-Dimensional Porous Polymer Matrices," *Biochem. Biophys. Res. Commun.* 213:639-644 (1995).

Attawia et al., "The Long Term Osteoblast Response to Poly (Anhydride-Co-Imides): A New Degradable Polymer for Use in Bone," *Fifth World Congress*, May 29-Jun. 2, 1996, Toronto, Canada.

Barton et al., "Surface and Bulk Properties of Amorphous Calcium Phosphate," *Colloid Interface Sci.* [Proc. Int. Conf.], $50^{th}$ 3:71, 1976, [CA 87:73954v].

Benghuzzi et al., "Resorbable and Biodegradable Ceramics as Drug Delivery Systems," 8th Southern Biomedical Engineering Conference, Richmond, VA, Oct. 15-16, 1989; Biomater. Artif. Cells. Artif. Organs., 17:463 (1989).

Benghuzzi et al., "Alcap Ceramic Implantable Devices and the Effect of Surface Area on the Delivery of Various Steroid Hormones," 8th Southern Biomedical Engineering Conference, Richmond, VA, Oct. 15-16, 1989; Biomater. Artif. Cells Artif. Organs, 17:463 (1989).

Benghuzzi et al., "Long-Term Delivery of Danazol by Biodegradable Ceramic Devices," 8th Southern Biomedical.Engineering Conference, Richmond, VA, Oct. 15-16, 1989; Biomater. Artif. Cells Artif. Organs, 17:463 (1989).

Benghuzzi et al., "Controlled Release of Hydrophilic Compounds by Resorbable and Biodegradable Ceramic Drug Delivery Devices," *Biomed. Sci. Instrum.* 28:179-182 (1992).

Besic et al., "Electron Probe Microanalysis of Noncarious Enamel and Dentin and Calcified Tissues in Mottled Teeth," *J. Dent. Res.* 48:131-139 (1969).

Blumenthal et al., "Effect of Preparation Conditions on the Properties and Transformation of Amorphous Calcium Phosphate," *Mater. Res. Bull.* 7:1181 (1972).

Boskey, "Matrix Proteins and Mineralization: An Overview," *Connect. Tissue Res.* 35:357-363 (1996).

Brown et al., "Phase Relationships in the Ternary System $CaO-P_2O_5-H_2O$ at 25°C.," *J. Am. Ceram. Soc.* 75:17-22 (1992).

Budavari et al., "Doxorubicin," *The Merck Index, an Encyclopedia of Chemicals, Drugs, and Biologicals*, Twelfth ed, pp. 581-582 (1996).

Cannon et al., "Continuous Delivery of Azidothymidine by Hydroxyapatite or Tricalcium Phosphate Ceramics," *Biomed. Sci. Instrum.* 31:159-164 (1995).

Chen et al., "Isolation and Characterization of Osteoprogenitors From Adult Murine Long Bone," *Orthoped. Res. Soc.*, $43^{rd}$ Annual Mtg., San Francisco, CA:15-3 (1997).

Chu et al., "Articular Cartilage Repair Using Allogeneic Perichondrocyte-Seeded Biodegradable Porous Polylactic Add

(56) References Cited

OTHER PUBLICATIONS (PLA): A Tissue-Engineering Study," *J. Biomed. Mater. Res.* 29:1147-1154 (1995).
Chung et al., "Biological Effects of Drug-Loaded Biodegradable Membranes for Guided Bone Regeneration" *J. Periodont. Res.* 32:172-175 (1997).
Clarke et al., "Non-Steroidal Anti-Inflammatory Drug Induced Differentiation of Bone Marrow Stromal Cells" *Orthoped. Res. Soc.*, 43rd Ann. Mtg., San Francisco, CA:574 (1997).
Constant et al., "Skeletal Repair by in Situ Formation of the Mineral Phase of Bone," *Science* 267:1796-1798.
Covey et al., "Clinical Induction of Bone Repair with Demineralized Bone Matrix or a Bone Morphogenetic Protein," *Orthop. Rev.* 18:857-863 (1989).
Denissen et al., "Net-Shaped Hydroxyapatite Implants for Release of Agents Modulating Periodontal-Like Tissues," *J. Periodontal Res.* 32:40-46 (1997).
Driessens et al., "Calcium Phosphate Bone Cements," *Encyc. Hand. Biomat. Bioeng.*, pp. 855-877 (1995).
Ducheyne et al., "Bioceramic Composites," *In An Introduction to Bioceramics, Advanced Series in Ceramics*, vol. I, Chapter 15(1993).
Eanes et al., "Intermediate States in the Precipitation of Hydroxyapatite," *Nature* 208:365-367 (1965).
Eanes et al. "Intermediate Phases in the Basic Solution Preparation of Alkaline Earth Phosphates," *Calcif. Tissue Res.* 2:38-48 (1968).
Eanes, "Thermochemical Studies on Amorphous Calcium Phosphate," *Calcif. Tissue Res.* 5:133-145 (1970).
Elgendy et al., "Osteoblast-Like Cell (MC3T3-E1) Proliferation on Bioerodible Polymers: An Approach Towards the Development of a Bone-BioErodible Polymer Composite Material," *Biomater.* 14:263-169 (1993).
Etex (Knaack et al.), "Novel fully Resorbable Calcium Phosphate Bone Substitue," *1997 ASBMR Abstract;* vol. 12, Supplement 1, s202 (Aug. 1997).
Etex (Knaack), "Endothermically Setting Calcium Phosphate Bone Substitute," *Orthopaedic Congress*, Aug. 20-22, 1997, Boston MA.
Etex (Knaack et al.), "A Fully Resorbable Calcium Phosphate Bone Substitute," *Portland Bone Symposium* (1997).
Fabbri et al., "Hydroxapatite-Based Porous Aggregates: Physico-Chemical Nature, Structure, Texture and Architecture," *Biomaterials* 16:225-228 (1995).
Freed et al., "Cultivation of Cell-Polymer Cartilage Implants in Bioreactors," *J. Cellular Biochemistry* 51:257-264 (1993).
Freed et al., "Biodegradable Polymer Scaffolds for Tissue Engineering," *Biotech.* 12:689-693 (1994).
Glimcher et al., "Recent Studies of Bone Mineral: Is the Amorphous Calcium Phosphate Theory Valid," *J. Crystal Growth* 53:100-119 (1981).
Glimcher, "Recent Studies of the Mineral Phase in Bone and its Possible Linkage to the Organic Matrix by Protein-Bound Phosphate Bonds," *Philos. Trans. R. Soc. Lond. B. Biol. Sci.* 304:479-508 (1984).
Glowacki et al., "Demineralized Bone Implants," *Clin. Plast. Surg.* 12:233-241 (1985).
Goto et al., "Studies on the Toxicities of Aluminum Hydroxide and Calcium Phosphate as Immunological Adjuvants for Vaccines," *Vaccine* 11:914-918 (1993).
Goto et al., "Local Tissue Irritating Effects and Adjuvant Activities of Calcium Phosphate and Aluminum Hydroxide with Different Physical Properties," *Vaccine* 15:1364-1371 (1997).
Graves et al., "Resorbable Ceramic Implants," *J. Biomed. Mater. Res. Symposium* 2:91 (1971).
Greene et al., "Stability of Cisplatin in Aqueous Solutions," *Am. J. Hosp. Pharma.* 36:38-43 (1979).
Greenfield et al., "Formation Chemistry of Amorphous Calcium Phosphates Prepared from Carbonate Containing Solutions,"*Calcif. Tissue Res.* 9:152-162 (1972).
Gupta et al., "Adjuvants—A Balance Between Toxicity and Adjuvanticity," *Vaccine* 11:293-306 (1993).

Gupta et al., "Comparison of Adjuvant Activities of Aluminum Phosphate, Calcium Phosphate and Stearyl Tyrosine for Tetanus Toxoid," *Biologicals* 22:53-63 (1994).
Gupta et al. "Adjuvant Properties of Aluminum and Calcium Compounds," *Vaccine Design*, Chapter 8, p. 229-248 (1995).
Hirasawa et al., "Manufacture of High Purity Hydroxyapatite," *Chemical Abstracts*, 108:166, No. 78193h (Mar. 7, 1988).
Holmes et al., "Surface Areas by Gas Adsorption on Amorphous Calcium Phosphate and Crystalline Hydroxyapatite,"*Calc. Tissue Res.* 7:163-174 (1971).
Hubbell, "Biomaterials in Tissue Engineering." *Biotech.* 13:565-576 (1995).
Ickovic et al., "Calcium-Phosphate-Adjuvanted Allergens: Total and Specific IgE Levels Before and After Immunotherapy with House Dust and Dermatophagoides pteronyssinus Extracts," *Ann. Immunol.* 1340:358-398 (1983).
Ijntema et al., "Hydroxyapatite Microcarriers for Biocontrolled Release of Protein Drugs," *Int'l. J. Pharm.* 112:215, (1994).
Ikada et al., "Release of Antibiotic from Composites of Hydroxyapatite and Poly(lactic acid)," *J. Control. Release* 2:179 (1985).
Ishaug et al., "Osteoblast Function on Synthetic Biodegradable Polymers," *J. Biomed. Mater. Res.* 28:1445-1453 (1994).
Ishikawa et al. "Effects of Preparation in Aqueous Solution on Properties of Hydroxyapatites," *Dent. Mater. J.* 9:58-69 (1990).
Itokazu et al., "Drug Delivery Systems using Porous Hydroxyapatite Blocks," *J. Orthopaedic Surgery* 2:47 (1994).
Jang, "Advanced Polymer Composites," *In the Materials Information Society*, Chap 1 (1994).
Kato et al., "Relationship Between Hemolytic Activity and Adsorption Capacity of Aluminum Hydroxide and Calcium Phosphate as Immunologic Adjuvants for Biologicals," *Microbiol. Immunol.* 38:543-548 (1994).
Kim et al., "Effect of Recombinant Human (1-84) Parathyroid Hormone on Fracture Healing in Ovariectomized Rat," *Orthoped. Res. Soci., 43rd* Ann. Meeting., San Francisco, CA:181-31 (1997).
Knaack et al, "Novel Fully Resorbable Calcium Phosphate Bone Substitute," 1997 ASBMR Abstract; vol. 12, Supplement 1, Aug. 1997, pp. s202.
Knaack, "Endothermically Setting Calcium Phosphate Bone Substitute," *Orthopaedic Congress*, Aug. 20-22, 1997, Boston MA.
Knaack et al, "A Fully Resorbable Calcium Phosphate Bone Substitute," *Portland Bone Symposium* (1997).
Kossovsky et al., "Surface-Modified Nanocrystalline Ceramics for Drug Delivery Applications," *Biomaterials* 15:1201-1207 (1994).
Kossovsky et al., "Preservation of Surface-Dependent Properties of Viral Antigens Following Immobilization on Particulate Ceramic Delivery Vehicles," *J. Biomed. Mat. Res.* 29:561-573 (1995).
Kreuter et al., "Influence of the Particle Size on the Adjuvant Effect of Particulate Polymeric Adjuvants," *Vaccine* 4:125-129 (1986).
Labarthe et al., "Sur la Structure et les Propriétés des Apatites Carbonatées de Type B Phospho-Calciques," *Ann. Chem.* 8:289 (1973).
Mileti et al., "Development of a Hydroxyapatite Ceramic Matrix for Continuous Delivery of Coumadin," *Biomed. Sci. Instrum.* 31:177-182 (1995).
Moldovan et al., "A Ceramic System for Continuous Release of Acetylsalicylic Acid," *Biomed. Sci. Instrum.* 30:175-180 (1994).
Moldovan et al., "Continuous Delivery of Analgesics by Ceramics," Abstract, Fifth World Biomaterials Congress, Toronto, Canada, Jun. 2, 1996.
Nolan et al., "Calcium Hydroxyapatite Ceramic Delivery System," *J. Bone Joint Surg. Br.* 75:334-335 (1993).
Norian Corporation, Product Information Sheet, "The Material Science of Norian SRS™, Skeletal Repair System™," Fall (1997).
Nylen et al., "Molecular and Ultrastructural Studies of Non-Crystalline Calcium Phosphates," *Calcif. Tissue Res.* 9:95-108 (1972).
Onodera et al., "Identification of Macrophage Migration Inhibitory Factor in Murine Neonatal Calvarie and Osteoblasts," 43rd Annual Meeting, Orthopaedic Research Society, San Francisco, CA, 322, Feb. 9-13, 1997.

(56) References Cited

OTHER PUBLICATIONS

Otsuka et al., "Drug Release Behavior from Self-Setting Calcium Phosphate Cement Containing Anti-Cancer Drug," *Proceedings of the Controlled Release Society* 21:268-269 (1994).
Otsuka et al., "A Novel Skeletal Drug Delivery System Using Self-Setting Calcium Phosphate Cement. 4: Effects of the Mixing Solution Volume on the Drug Release Rate of Heterogeneous Aspirin-Loaded Cement," *J. Pharm. Sci.* 83:259-263 (1994).
Otsuka et al., "Effect of Particle Size of Metastable Calcium Phosphates on Mechanical Strength of a Novel Self-Setting Bioactive Calcium Phosphate," *J. Biomed. Mater. Res.* 29:25-32 (1995).
Otsuka et al., "A Novel Skeletal Drug Delivery System Using Self-Setting Calcium Phosphate Cement. 9: Effects.Of the Mixing Solution Volume on Anticancer Drug Release from Homogeneous Drug-Loaded Cement," *J. Pharm. Sci.* 84:733-736 (1995).
Pool, "Coral Chemistry Leads to Human Bone Repair," *Science* 267:1772 (1995).
Posner et al., "Synthetic Amorphous Calcium Phosphate and its Relation to Bone Mineral Structure," *Bone Mineral Structure,* vol. 8, p. 273-281 (1975).
Relyveld, "Current Developments in Production and Testing of Tetanus and Diphtheria Vaccines," *New Developments with Human and Veterinary Vaccines,* pp. 51-76 (1980).
Relyveld et al., "Calcium Phosphate Adjuvanted Allergens," *Annals of Allergy* 54:521-529 (1985).
Relyveld et al., "Preparation and Use of Calcium Phosphate Adsorbed Vaccines," *Develop. Biol. Standard* 65:131-136 (1986).
Relyveld et al, "Humoral Response in Rabbits Immunized with Calcium Phosphate Adjuvanted HIV-1 gp160 Antigen," *Biomed. & Pharmacother..* 48:79-83 (1994).
Rey et al., "The Carbonate Environment in Bone Mineral: A Resolution-Enhanced Fourier Transform Infrared Spectroscopy Study," *Calcif. Tissue Int.* 45:157-164 (1989).
Rey et al., "Structural Studies of the Mineral Phase of Calcifying Cartilage," *J. Bone Miner. Res.* 6:515-525 (1991).
Rey et al., "Preparation of Microporous Ceramic at Low Temperature from Poorly Crystalline Apatite,"*Symposium Abstract* (1993).
Rey et al., "Chemical Properties of Poorly Crystalline Apatites," *Phosphorus Res. Bull.* 6:67-70 (1996). (Abstract).
Roodman, "Advances in Bone Biology: The Osteoclast," *Endocr. Rev.* 17:308-322 (1996).
Rozencweig et al., "Cis-Diannminedichloroplatinum (II): A New Anticancer Drug," *Annals Intern. Med.* 86:803-812 (1977).
Shinto et al., "Calcium Hydroxyapatite Ceramic Used as a Delivery System for Antibiotics," *J. Bone Joint Surg. Br.* 74:600-604 (1992).
Shors et al., "Porous Hydroxyapatite," *In an Introduction to Bioceramics,* eds. Hersch et al., Work Sci. Publ. Co. Pte. Ltd. (1993).
Termine et al., "Amorphous/Crystalline Interrelationships in Bone Mineral," *Calcif. Tissue Res.* 1: 8-23 (1967).
Thoma et al., "Biodegradable Gentamicin Depot-Implants Made of Beta-Tricalcium Phosphate Ceramics. 3: In Vivo Studies on Drug Release, Tissue Tolerance, and Biodegradation," *Pharmazie* 46:266-270 (1991).
Thoma et al., "Biodegradable Controlled Release Implants Based on β-Tricalcium Phosphate Ceramic," *Eur. J. Pharm. Biopharm.* 38:107-112 (1992).
Thomson et al., "Fabrication of Biodegradable Polymer Scaffolds to Engineer Trabecular Bone," *J. Biomater. Sci. Polym. Edn.* 7:23-28 (1995).
Törmälä, Biodegradable Self-Reinforced Composite Materials; Manufacturing Structure and Mechanical Properties, *Clin. Mater.* 10:29-34 (1992).
Tung et al., "An Intermediate State in Hydrolysis of Amorphous Calcium Phosphate," *Calcif. Tissue Int.* 35:783-790 (1983).
Tung, "In Vitro Drug Release of Antibiotic-Loaded Porous Hydroxyapatite Cement," *Artif. Cells Blood Substit. Immob. Biotech.* 23:81-88 (1995).
Uchida et al., "Slow Release of Anticancer Drugs from Porous Calcium Hydroxyapatite Ceramic," *J. Orthop. Res.* 10:440-445(1992).
Vassilev, "Aluminum Phosphate But Not Calcium Phosphate Stimulates the Specific IgE Response in Guinea Pigs to Tetanus Toxoid," *Allergy* 33:155-159 (1978).
Yamamura et al., "Antitumor Effects and Distributions of Adriamycin Incorporated Into Hydroxyapatite Implants in a Cancer Rat Model Bearing Swarm Rat Chondrosarcoma," *Japan. J. Pharm.* 66:433-438 (1994).
Yamamura et al., "Anticancer Effects of Adriamycin-Loaded Hydroxyapatite Implants Determined in a Swarm Rat Chondrosarcoma Model," *Japan. J. Pharm.* 65:289-291 (1994).
Yasue et al., "Effect of Adsorption of Succinic Acid on the Formation of Amorphous Calcium Phosphate," *J. Ceramic Soc. Japan* (Japanese version), vol. 102, No. 12, pp. 1122-1127 (1994).

\* cited by examiner

CHEMOTHERAPEUTIC COMPOSITION USING NANOCRYSTALLINE CALCIUM PHOSPHATE PASTE

CROSS REFERENCE TO RELATED APPLICATIONS

This application is a continuation of application Ser. No. 09/693,120, filed Oct. 20, 2000, abandoned, which is a continuation-in-part of application Ser. No. 09/153,133, filed Sep. 15, 1998, pending, which is a continuation-in-part of application Ser. No. 08/729,342, filed Oct. 16, 1996, which issued as U.S. Pat. No. 6,541,037, each of which is incorporated by reference.

BACKGROUND OF THE INVENTION

The present invention relates to pharmaceutical compositions and methods for the treatment of cancer.

Following surgical removal or radiation therapy for the removal or reduction of hard and soft tissue tumors, patients are faced with the possibility of persistent tumor cells, metastasis and tumor reoccurrence. In the case of bone tumors, patients face the additional problem of poor mechanical integrity of the bone. Cancer patients typically receive postoperative chemotherapy to reduce the chances of tumor reoccurrence and metastasis. Chemotherapy also is used for the treatment of inoperable tumors. Systemically delivered anticancer drugs often produce severe side effects, such as liver toxicity, cardiotoxicity, hair and weight loss. Therapies often are discontinued or otherwise limited due to these adverse side effects.

While the effectiveness of chemotherapy has improved tremendously, the side effects associated with its administration remain a significant factor in patient mortality. Therefore, an important consideration when treating bone tumors and soft-tissue tumors with chemotherapeutic agents is maintaining a long-acting, yet highly effective concentration of the anticancer agent at the local site of the tumor while minimizing the often toxic systemic side effects.

MacroMed reports the use of a biodegradable polymer having reverse thermal gelation properties for intra-tumoral injections. Under the tradename OncoGel™, the poly(lactide-co-glycolide)-based polymer is deliverable through a small-gauge (25) needle and localized delivery is reported. See, U.S. Pat. No. 5,702,717 for further information on the polymeric material.

Hydroxyapatite is a major mineral in bone and teeth. It demonstrates excellent biocompatibility with bony tissue and has been used in the orthopedic industry as bone-filling material. Anticancer agents such as adriamycin, cis-platin and methotrexate have been incorporated into porous hydroxyapatite beads and blocks, and sustained release of the agents have been demonstrated. Administration of the drug-loaded blocks to a tumor site in a cancer rat model resulted in increased life span and reduction in body weight loss. See, Yamamura et al. *Jpn. J. Pharmacol.* 65:289 (1994); Yamamura et al. *Jpn. J. Pharmacol.* 66:433 (1994); and Uchida et al. *J. Orthop. Res.* 10(3):440 (1992).

However, hydroxyapatite ceramics typically are dense, highly crystalline materials, and as such, are poorly resorbable. Porosity must be engineered into the material to permit drug uptake during drug loading and drug release at the tumor site. Engineering of the hydroxyapatite block for a particular drug release profile is difficult and not easily reproducible. An additional limitation of use of a hydroxyapatite solid block or bead is that it requires surgical implantation.

Calcium phosphate cements are compositions having one or more dry components and a liquid which combine to form a material that is capable of setting into a solid calcium phosphate product. Materials that set into solid calcium phosphate mineral products are of particular interest as such products can closely resemble the mineral phase of natural bone, are potentially remodelable, and are biocompatible.

Patents of interest describing calcium phosphate cements include: U.S. Pat. No. 4,684,673 to Adachi et al.; U.S. Pat. No. 5,037,639 to tung et al., U.S. Pat. Nos. 5,683,461, 5,676,976 and 5,650,176 to Lee et al; U.S. Pat. Nos. 4,108,690, 5,968,253 to Posner et al. and U.S. Pat. No. 5,508,342 to Antonucci et al, as well as U.S. Pat. Nos. 4,880,610, 5,047,031, 5,129,905, 5,336,264, 5,053,212, 5,178,845, and 5,580,623 to Constantz et al.; U.S. Pat. Nos. 5,569,442 and 5,571,493 to Fulmer et al.; and U.S. Pat. Nos. 5,496,399; 5,683,667; 5,683,496; and 5,697,981 to Ison et al. Also of interest are WO 96/36562 and WO 97/17285.

Constantz et al., "Skeletal Repair by in Situ Formation of the Mineral Phase of Bone," Science (Mar. 24, 1995) 267: 1796-1798, describes a calcium phosphate cement comprising α-tricalcium phosphate, monocalcium phosphate monohydrate (MCPM), and $CaCO_3$. Also of interest is Otsuka et al. "A Novel Skeletal Drug Delivery System Using Self-Setting Calcium Phosphate Cement. 9: Effects of the Mixing Solution Volume on Anticancer Drug Release from Homogeneous Drug-loaded Cement" *J. Pharm. Sci.* 84(6):733 (June 1995), which describes a calcium phosphate cement made up of tetraclacium phosphate (TTCP) and dicalcium diphosphate (DCPD) and incorporating the anticancer agent 6-mercaptopurine (6-MP). The addition of 6-MP was reported not to interfere with the setting properties of the cement; however, the drug release profile form the cement was not acceptable, presumably due to crystallization of the calcium phosphate cement with time. The effectiveness of cement as a delivery system was not established, as only model in vitro release studies were reported.

A number of these calcium phosphate cements suffer from one or more drawbacks, such as low resorbability, rapid set time, poor flow characteristics and inability to provide controlled release of an active agent. None of the calcium phosphate cements report setting times and material flow characteristics which are amenable to injection or cannulation.

Thus, there is a need for an anticancer agent delivery system that combines desirable delivery characteristics (e.g. resorbability, controlled release, biocompatibility) in conjunction with the ability to be injectable, and thus able to administer the therapeutic mixture by syringe or cannula.

There remains a need for a drug delivery system that slowly releases an anticancer agent exclusively into the tumor.

There remains a further need for a drug delivery system that is easy to administer to the tumor site with minimum trauma to the patient.

SUMMARY OF THE INVENTION

The present invention provides a nanocrystalline or poorly crystalline calcium phosphate composition for use in the local treatment of cancer. The composition demonstrates excellent biocompatibility, controlled drug release and ease of administration. The composition readily incorporates the drug with simple mixing and can be administered without invasive surgery by injection or by cannula. The setting and crystallization properties of the composition are not significantly affected by the addition of a therapeutic agent. The nanocrystalline or poorly crystalline features of the calcium phosphate carrier provide ideal drug delivery and bioresorption profiles.

In one aspect of the invention, a method for treating cancer in a mammal is provided, in which an anticancer composition is administered to a tumor site of the mammal. The composition includes a mixture of an anticancer agent and a calcium phosphate paste, and the paste includes one or more nanocrystalline or poorly crystalline calcium phosphates and a physiologically acceptable fluid. The paste has an injectable or formable consistency at the time of administration and is hardenable at the tumor site.

In one embodiment, each calcium phosphate has a Ca/P ratio of less than or equal to 1.7.

In another embodiment, the anticancer agent is selected from the group consisting of methotrexate, cis-platin, prednisone, hydroxyprogesterone, medrioxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, mephalan, uracil mustard, chlorambucil, busulfan, carmustine, lomusline, dacarbazine (DTIC, dimethyltriazenomideazolecarboxamide), fluorouracil, 5-fluorouracil, cytarabine, cytosine arabinoxide, mercaptopurine, 6-mercaptomurine, tamoxifan, paclitaxel, etopiside, vinorelbine, gemcitabine, leuprolide, flutamide, goseralin acetate, and thioguanine, and mixtures thereof.

In another embodiment, the anticancer composition is administered to the tumor site by cannula or by injection, or the anticancer composition is administrable by cannula or injection more than five minutes after its preparation, or the anticancer composition is administrable by cannula or injection more than twenty minutes after its preparation.

In still another embodiment, the paste hardens into an apatitic calcium phosphate.

In some embodiments, the nanocrystalline or poorly crystalline calcium phosphate paste comprises a calcium phosphate selected from the group consisting of poorly crystalline apatitic (PCA) calcium phosphates (PCA), dicalcium phosphates, such as dicalcium phosphate dihydrate (DCPD) and dicalcium phosphate anhydrous (DCPA), tricalcium phosphates (TCP), monetite, monocalcium phosphate monohydrate (MCPM), hetpacalcium phosphate, calcium pyrophosphate, calcium metaphosphate, octacalcium phosphates (OCP), hydroxyapatites (HA), or at least one of the nanocrystalline or poorly crystalline calcium phosphates is a poorly crystalline apatitic calcium phosphate.

In some embodiments, each of the one or more nanocrystalline or poorly crystalline calcium phosphates has a calcium to phosphate ratio in the range of 1.0 to 1.67, or in the range of 1.3 to 1.67.

In other embodiments, the nanocrystalline or poorly crystalline calcium phosphate paste has an overall calcium to phosphate ratio in the range of 1.0 to 1.7, or in the range of 1.40 to 1.65.

In some embodiments, the nanocrystalline or poorly crystalline calcium phosphate paste comprises a physiologically acceptable fluid in an amount sufficient to produce a paste having injectable or formable consistency.

In still other embodiments, a therapeutically effect amount of anticancer agent is released from the composition for a time greater than one week, or for a time greater than two week, or for a time greater than one month, or for a time greater than three months.

In yet another embodiment, delivery of the anticancer therapy to the tumor site is sufficient to prevent increase of tumor mass without significant weight loss of the mammal, or delivery of the anticancer therapy to the tumor site is sufficient to result in a decrease in tumor mass without significant weight loss in the mammal.

In still another embodiment, the particle size of the nanocrystalline or poorly crystalline calcium phosphate is selected to provide a desired release kinetic of the anticancer drug.

In another aspect of the invention, an anticancer composition includes a mixture of a physiologically effective amount of an anticancer agent and a calcium phosphate paste including one or more nanocrystalline or poorly crystalline calcium phosphate and a physiologically acceptable fluid. The paste has an injectable or formable consistency at the time of administration and hardenable at the tumor site.

In one embodiment, each calcium phosphate having a Ca/P ratio of less than or equal to 1.7.

In another embodiment, the anticancer agent is selected from the group consisting of methotrexate, cis-platin, prednisone, hydroxyprogesterone, medrioxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, mephalan, uracil mustard, chlorambucil, busulfan, carmustine, lomusline, dacarbazine (DTIC, dimethyltriazenomideazolecarboxamide), fluorouracil, 5-fluorouracil, cytarabine, cytosine arabinoxide, mercaptopurine, 6-mercaptomurine, tamoxifan, paclitaxel, etopiside, vinorelbine, gemcitabine, leuprolide, flutamide, goseralin acetate, and thioguanine, and mixtures thereof In still other embodiments, the nanocrystalline or poorly crystalline calcium phosphate cement comprises a calcium phosphate selected from the group consisting of amorphous calcium phosphate, poorly crystalline apatitic (PCA) calcium phosphates (PCA), dicalcium phosphates, such as dicalcium phosphate dihydrate (DCPD) and dicalcium phosphate anhydrous (DCPA), tricalcium phosphates (TCP), monetite, monocalcium phosphate monohydrate (MCPM), hetpacalcium phosphate, calcium pyrophosphate, calcium metaphosphate, octacalcium phosphates (OCP), hydroxyapatites (HA), or at least one of the nanocrystalline or poorly crystalline calcium phosphates is selected from the group consisting of amorphous calcium phosphate and poorly crystalline apatitic calcium phosphate.

In some embodiments, each of the one or more nanocrystalline or poorly crystalline calcium phosphates has a calcium to phosphate ratio in the range of 1.3 to 1.67, or the nanocrystalline or poorly crystalline calcium phosphate paste has an overall calcium to phosphate ratio in the range of 1.0 to 1.7, in the range of 1.0 to 1.67 or in the range of 1.40 to 1.65.

In other embodiments, the anticancer composition is of a consistency administrable to the tumor site by cannula or by injection.

In other embodiments, the nanocrystalline or poorly crystalline calcium phosphate paste comprises a physiologically acceptable fluid in an amount sufficient to produce a paste having injectable or formable consistency for at least five minutes, or for at least twenty minutes.

In still other embodiments, the nanocrystalline or poorly crystalline calcium phosphate paste is hardenable into an apatitic calcium phosphate.

In yet other embodiments, a therapeutically effect amount of anticancer agent is released from the composition for a time greater than one week, or for a time greater than two week, or for a time greater than one month, or for a time greater than three months.

In still another embodiment, delivery of the anticancer therapy to the tumor site is sufficient to at least prevent increase of tumor mass without significant weight loss of the mammal, or delivery of the anticancer therapy to the tumor site is sufficient to prevent a decrease in tumor mass without significant weight loss in the mammal.

In yet another embodiment, the particle size of the calcium phosphate is selected to provide a desired release kinetic of the anticancer drug.

In still another aspect of the invention, a kit for use in preparing a flowable anticancer composition that remain injectable for at least about 20 minutes is provided. The kit includes dry ingredients having a nanocrystalline or poorly crystalline calcium phosphate and a second calcium phosphate in a proportion of about 1:10 to 10:1 by weight; a physiologically acceptable aqueous lubricant in an amount sufficient to produce a flowable product upon combination with the dry ingredients; and an anticancer agent in an amount ranging from about 0.01 to 10 wt. % of the dry ingredients.

In one embodiment, the kit further includes a means of mixing the dry ingredients and the lubricant, or an injecting means.

By "nanocrystalline calcium phosphate (NCP)" is meant a calcium phosphate solid which exhibits crystalline domains on the order of nanometers or Angstroms. NCP materials may include localized structure based upon well-known calcium phosphates, such as hydroxyapatite, tricalcium apatite, octacalcium phosphate, etc.; however, long-range order is substantially absent. Exemplary NCP materials based upon hydroxyapatite are found in U.S. Pat. No. 5,783,217.

By "poorly crystalline apatitic (PCA) calcium phosphate" is meant a synthetic calcium phosphate of apatitic structure demonstrating only short-range crystallinity. The PCA calcium phosphate is not necessarily restricted to a single calcium phosphate phase, provided is demonstrates the characteristic X-ray diffraction pattern of an apatitic mineral, namely two broad peaks in the region of 20-35° with a peak centered at 26° and a second peak centered at 32°. Exemplary PCA calcium phosphate materials are found in U.S. Ser. No. 08/729,342, hereby incorporated by reference.

BRIEF DESCRIPTION OF THE DRAWING

The invention is described with reference to the following drawings which are presented for the purpose of illustration only, which are not intended to be limiting of the invention, and in which.

DESCRIPTION OF THE PREFERRED EMBODIMENTS

Figure 1:
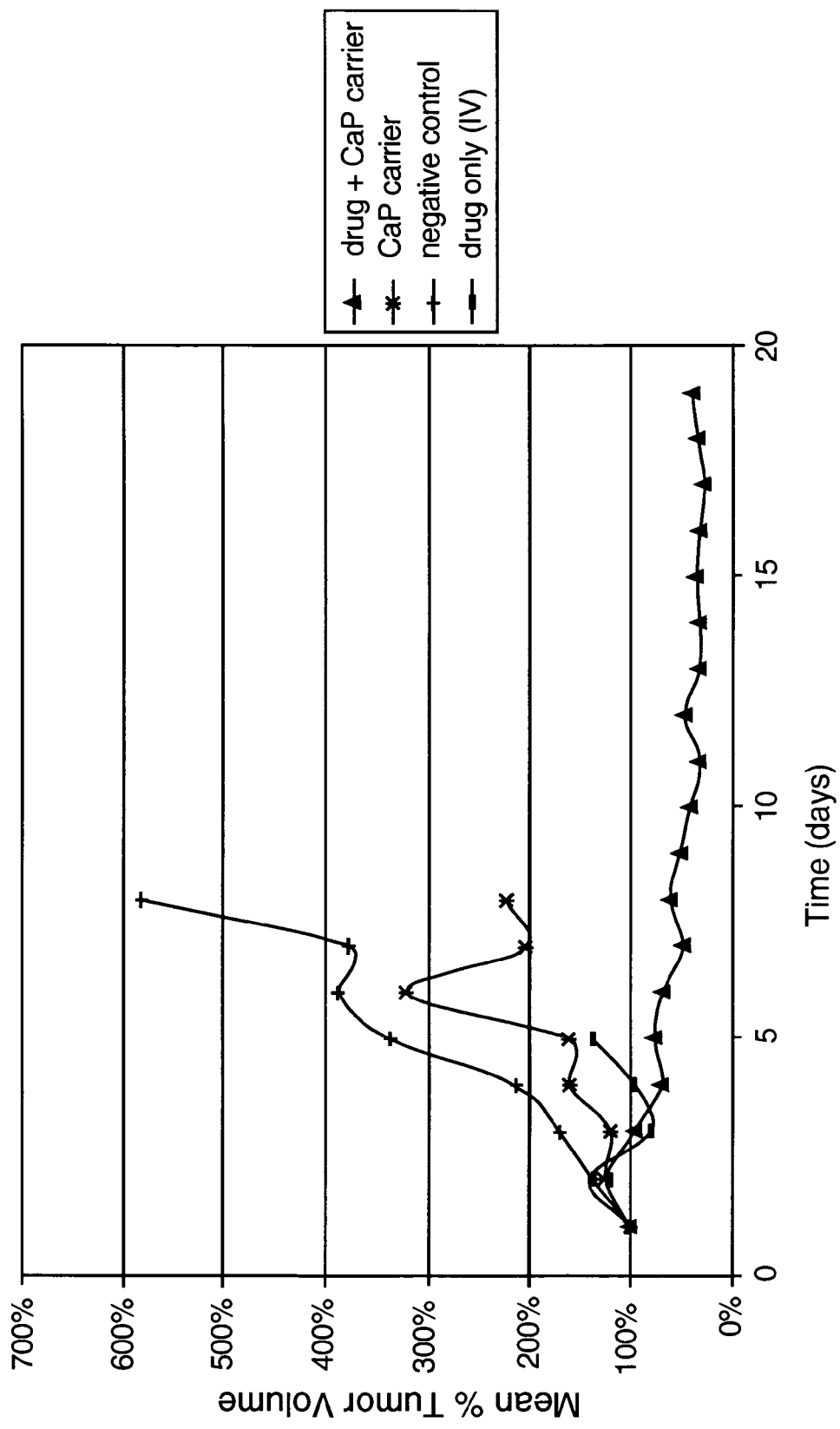
FIG. 1 is a plot of the % tumor mass change over time in C3H mice for 25 mg/kg cisplatin dose in calcium phosphate delivery vehicle (▲), calcium phosphate delivery vehicle alone (*), no treatment (+), and systemic IV administration of cisplatin (−)

The nanocrystalline calcium phosphate composition of the invention demonstrates excellent biocompatibility, controlled drug release and ease of administration. The composition readily incorporates the drug with simple mixing and can be administered without invasive surgery by injection or by cannula. The flowable material may be injected into a cancellous bone void and the material sets into a solid calcium phosphate product that is capable of withstanding physiological loads, making such products extremely attractive for use in the treatment of bone tumors. The composition may similarly be injected into soft-tissue tumors. The flowable nature of the calcium phosphate composition of the invention allows the mixture to flow around and into the tumor, where it hardens into a calcium phosphate cement. The tumor may be encapsulated thereby in the hardened calcium phosphate cement which confines the cancer cells of the tumor and helps to prevent metastasis.

The calcium phosphate paste may include any nanocrystalline or poorly crystalline calcium phosphate material in which the chemical composition and material properties have been selected to provide the desired flow properties and bioresorption. The desired flow properties include the ability to deliver the calcium phosphate composition by syringe or cannula. The paste is considered "injectable" if it is capable of passing through a 16 gauge needle. In preferred embodiments, injectability is maintained after storage, for example, for one minute, five minutes, ten minutes and most preferably 30 minutes. Injectability is evaluated by determining the ability to inject 1 cc of paste material through a 16 gauge needle or smaller, with only finger or hand pressure being applied by the user. The material is capable of injection through small gauge needles, e.g., 18-gauge to 25-gauge needles.

The paste is made up of a dry powder component, a liquid component and an anticancer agent.

The dry component includes one or more nanocrystalline calcium phosphates. Each calcium phosphate has a calcium to phosphate (Ca/P) ratio of less than or equal to 1.7, and preferably a Ca/P ratio in the range of 1.0-1.65. Calcium phosphates of interest include, but are not limited to, calcium phosphates such as poorly crystalline apatitic (PCA) calcium phosphates (PCA), dicalcium phosphates, such as dicalcium phosphate dihydrate (DCPD) and dicalcium phosphate anhydrous (DCPA), tricalcium phosphates (e.g., α- and β-TCPs), monetite, monocalcium phosphate monohydrate (MCPM), hetpacalcium phosphates, calcium pyrophosphates, calcium metaphosphates, octacalcium phosphates (OCP), hydroxyapatites (HA), which are nanocrystalline or poorly crystalline in nature. Other calcium phosphates are described by Driessen (1995), which is hereby incorporated by reference. Carbonated or otherwise substituted versions of these calcium phosphates are also contemplated in the invention. Calcium deficient or poorly crystalline apatitic calcium phosphates having a Ca/P ratio of about 1.0-1.65, preferably 1.0-1.6, or 1.0-1.5 or 1.0-1.4, or 1.50-1.65, and more particularly 1.55-1.65, are preferred. Another preferred calcium phosphate is nanocrystalline calcium phosphate (NCP), in particular a hydroxyapatitic NCP.

The preferred nanocrystalline calcium phosphates, NCP, or PCA calcium phosphate, may be used alone, or in combination with each other, or individually with a second calcium phosphate to form the dry component of the composition. Suitable second calcium phosphates are those which are capable of reacting with the primary calcium phosphate to form a hardened cement. Exemplary calcium phosphates include dicalcium phosphates, such as dicalcium phosphate dihydrate (DCPD) and dicalcium phosphate anhydrous (DCPA), tricalcium phosphates (TCP), monetite, monocalcium phosphate monohydrate (MCPM), hetpacalcium phosphate, calcium pyrophosphate, calcium metaphosphate, octacalcium phosphates (OCP), hydroxyapatites (HA). A preferred dry powder combination is a nanocrystalline calcium phosphate and dicalcium phosphate, e.g., DCPD. Another preferred embodiment is a poorly crystalline apatitic calcium phosphate and a dicalcium phosphate. A detailed description of the preparation and characteristics of suitable calcium phosphates can be found in U.S. Pat. No. 5,783,217, which is hereby incorporated by reference.

A particularly preferred dry component is a combination of calcium phosphate powders which react to form an apatitic calcium phosphate. Hydroxy apatite is the mineral component of naturally-occurring bone having a Ca/P ratio of 1.67, although the actual Ca/P ratio of bone varies between 1.5 and 1.7. The composition and relative amounts of the dry powder components preferably are selected to provide an overall Ca/P ratio in the range of 1.0-1.7, or 1.3-1.65, or 1.4-1.6, or preferably close to that of naturally-occurring bone, that is in the range of 1.45 to 1.7. It has been observed that calcium-deficient compositions exhibit more rapid, resorption characteristics. In some embodiments where rapid resorption is desired, it may be desired to use select dry powder components to provide an overall Ca/P ratio of less than 1.67, and preferably in the range of 1.4 to 1.65.

The composition of the invention also includes one or more anticancer agents. The anticancer agent may be introduced with the powder component, or with the liquid component of the composition, or it may be separately added to the composition. Suitable anticancer agents may be one or more of known chemotherapy drugs such as methotrexate, cis-platin, prednisone, hydroxyprogesterone, medrioxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, mephalan, uracil mustard, chlorambucil, busulfan, carmustine, lomusline, dacarbazine (DTIC, dimethyltriazenomideazolecarboxamide), fluorouracil, 5-fluorouracil, cytarabine, cytosine arabinoxide, mercaptopurine, 6-mercaptomurine, tamoxifan, paclitaxel, etopiside, vinorelbine, gemcitabine, leuprolide, flutamide, goseralin acetate, and thioguanine, and mixtures thereof.

Exemplary anticancer agents and the suggested dosage are found in Table 1. The amount of anticancer agent that is present in the cement will be sufficient to provide a composition that at least prevents tumor growth in the region where the composition has been introduced as compared to a control. In preferred embodiments, the amount and effectiveness of the anticancer agent is sufficient to reduce the tumor size or even to substantially eliminate the tumor.

TABLE 1

| Cancer | Drug | Mechanism of action | Dosage | response rate |
|---|---|---|---|---|
| Breast | tamoxifan | non-steroidal antiestrogen; inhibits binding of estrogen to receptors | 20 mg/daily (tablet) | as 1$^{st}$ line hormonal therapy; 60% steroid receptor cancers respond |
| | doxorubicin | inhibits action of topoisomerase II; forms free radicals, binds to membrane | 60-75 mg/m$^2$ IV (every 21 days) | none known |
| | methotrexate | inhibitor of dihydrofolate reductase; interferes with cellular enzymes | 30-40 mg/m$^2$ IV (once a week) | with cyclophosphamide and 5-fluorouracil, 30-50%) |
| | cyclophosphamide | alkylating agent; crosslinks DNA and RNA strands, prevents cell division | 50-1000 mg/m$^2$; 1× treatment | 35% alone, 90% combination therapy |
| | 5-fluorouracil | effects DNA and RNA | 500 mg/m$^2$, 1× day, repeat 4-5 wk | partial remission 10-20% |
| | paclitaxol | stabilizes microtubule formation leading to cell death | 175 mg/m$^2$, (every three weeks) | 56-62% response in previously treated patients |
| small cell lung | etoposide (+cisplatin) | interferes with DNA synthesis by interacting with topoisomerases II | 80/m$^2$ for three days | 30-35% alone; 50% with cisplatin |
| non-small cell lung | paclitaxol (+cisplatin) | interferes with DNA synthesis by interacting with topoisomerases II | 80 mg/m$^2$ for three days | mg 34-40% in previously untreated patients |
| | vinorelbine (+cisplatin) | antitubulin, causes miotic arrest in G2 and M phases | 30 mg/m$^2$ for 3 days | 33% alone; 28% with cisplatin |
| | gemcitabine (+cisplatin) | affects cell undergoing DNA syntheses and blocks progression through G1/S | not given in lungs | not given in lungs |
| prostate | leuprolide | desensitizes LH-RH receptors and reduces release of hormones | 7.5 mg im, 1× month | survival favored for leuprolide/flutamide combination |
| | goseralin acetate | down regulates LH-RH receptor, medical castration, reduces testosterone | 3.6 mg s.c., 1× month | with flutamide 70% |

TABLE 1-continued

| Cancer | Drug | Mechanism of action | Dosage | response rate |
|---|---|---|---|---|
| | flutamide | nonsteroid antiandrogen, used with LH-RH analogue | 250 mg, every 8 h, orally | 70% combination therapy |
| | diethylestilbestrol | synthetic estrogen | 1-3 mg, daily | 65% |

In other embodiments, two or more anticancer agents are included in the composition. Certain combination therapies have been identified as particularly effective and are found in Table 2. The amount of anticancer agent that is present in the cement will generally range from about 0.01 to 10, usually from about 0.01 to 5.0 and more usually from about 0.01 to 3.0% by weight of the dry ingredients of the cement.

TABLE 2

| Cancer | combination therapy |
|---|---|
| breast | 5-fluorouracil, doxorubicin (>60 mg/m$^2$), cyclophophamide cyclophosphamide, doxorubicin (<60 mg/m$^2$), 5-fluorouracil cyclophosphamide, methotrexate, 5-fluorouracil doxorubicin, paclitaxol |
| small cell lung | cisplatin, etoposide |
| non-small cell lung | cisplatin, paclitaxol cisplatin, vinorelbine cisplatin, gemcitabin |
| prostate | leuprolide, flutamide goseraline acetate, flutamide |

Also provided are kits comprising the subject chemotherapeutic delivery vehicle, where the dry and liquid components may be present in separate containers in the kit, or some of the components may be combined into one container, such as a kit wherein the dry nanocrystalline or poorly crystalline calcium phosphate components are present in a first container and the liquid components are present in a second container. Instructions for use may also be included. The kit preferably includes dry ingredients comprising amorphous calcium phosphate, nanocrystalline or PCA calcium phosphate and a second calcium phosphate in a proportion of about 1:10 to 10:1 by weight, and preferably about 50:50 by weight; a physiologically acceptable aqueous lubricant (liquid component) in an amount sufficient to produce a flowable product upon combination with said dry ingredients; and an anticancer agent in an amount sufficient to produce the desired pharmaceutical effect and typically ranging from about 0.01 to 10 wt. % of said dry ingredients. Due to the need to carefully titrate the amount of anti-cancer agent based upon patient body mass and tumor size, the agent may be added separately. The agent may be added to the liquid component prior to mixing with the dry component, or it may be added to the injectable paste, once formed.

In preparing the subject calcium phosphate cements for use in the treatment of cancer, the dry components and the liquid components will be combined using any suitable means to produce a homogeneous, flowable paste-like material having the characteristics described above. One suitable means of combining the dry and liquid components is a mortar and pestle, with which the liquid and solid components are mixed to produce the flowable paste. Alternatively, one may employ an automated mixing device. See, U.S. Pat. No. 5,980,482, hereby incorporated by reference, for further description of a suitable mixing device.

Generally, the calcium phosphate composition is formed into an injectable gel or solid nanoparticle paste by the addition of a liquid component or lubricant. The liquid component is a physiologically acceptable liquid, such as but not limited to, water, saline, sodium phosphates, buffer solutions, serum, or tissue culture media. The liquid component may include one or more solutes, selected to buffer the liquid, stabilize the anti-cancer agent, or otherwise modify the properties of the calcium phosphate composition, e.g., modify reaction and hardening times or modify the composition or crystallinity of the product calcium phosphate. For example, sodium phosphate is typically used to accelerate the hardening of the calcium phosphate paste. The preferred calcium phosphate paste may be designed to absorb, bind, entrap or otherwise contain the anticancer agent.

The calcium phosphate cements, paste-like compositions and products are combined with an anticancer agent for its local delivery to a physiological site of interest. The calcium phosphate paste containing the anticancer agent remains formable and injectable at room temperature, facilitating the administration of the composition to a tumor site by injection or by cannula.

The calcium phosphate cement may be selected to set rapidly or slowly at room temperatures. In many instances it will be advantageous to have the calcium phosphate paste set slowly at room temperature, for example, to allow the medical professional adequate time to administer the therapeutic composition to the tumor site. For example, the calcium phosphate paste may remain flowable and injectable at room temperatures for a significant time, e.g., more than 5 minutes, more than 10 minutes, more than 20 minutes, and up to an hour. The calcium phosphate paste should nonetheless set rapidly under physiological conditions, e.g., less than 20 minutes, less than 10 minutes and preferably within 5 minutes. Thus, preferred calcium phosphate compositions exhibit a "dual setting" characteristic in that they are slow to set at about room temperature, e.g., 20-25 C, yet set rapidly at physiological temperatures e.g., 35-40 C. In such instances, a composition including PCA calcium phosphate as one of the components may be used.

In those instances where a more rapidly setting cement is desired, accelerators may be added to the composition. Exemplary accelerators include water-soluble sodium salts, such as sodium phosphate, sodium succinate, sodium lactate, sodium chloride, sodium acetate and the like.

Setting times may be determined using well-established standards, such as the Gillmore needle test (ASTM C 266-89 Standard Test Method of Time of Setting of Hydraulic-Cement Paste by Gillmore Needles) and the needle penetration test C 403/C 403M-95 Standard Test Method for Time of Setting of Concrete Mixtures by Penetration Resistance. The effect of the anticancer agent on the setting times may be determined using these tests as well.

Once in place, the paste hardens and releases the anticancer agent into the tumor environment over an extended period of time, relying on a combination of drug solubility and bioerosion of the calcium phosphate delivery vehicle. The calcium phosphate composition may be formulated to be resorbable over a preselected period of time. Calcium phosphate cements may be prepared which resorb within at least about 1 week, within about one month, within about one month and preferably within a year, so that the calcium phosphate cement may release the anticancer agent into their local environment for as long as is needed, depending on the specific cement from which the composition is prepared. Thus, the subject compositions find use as anticancer agent delivery vehicles, i.e. as anticancer agent depots, in which the local delivery of an anticancer agent for an extended period of time is desired. The subject compositions find particular use as local anticancer agent delivery vehicles for bone tissue, particularly cancellous bone tissue.

In most cases, the anticancer compositions are resorbable. Resorbable calcium phosphate cements biodegrade over time, ultimately leaving little or no residual material in the body. Resorbability generally eliminates the need for surgical removal of the delivery vehicle, after completion of chemotherapy.

Resorbable calcium phosphate cements also allow the controlled delivery of active agents to a the tumor site at a specific rate. The anticancer agent typically is delivered to a tumor site at a rate comparable to the resorption rate. Custom designed resorbability characteristics of the anticancer composition provides for selected delivery rates. In preferred embodiments, weakly resorbing calcium phosphate cements will be used to provide a slow release delivery of the anticancer agent to the tumor site. In other embodiments, the calcium phosphate cement will be strongly resorbable and provide a means to deliver a fast, quick dose of the anticancer agent to the tumor site. In yet other embodiments, a combination of weakly and strongly resorbable calcium phosphates will be used to produce a variable or pulsatile kinetic release. The resorption rate, and therefore the delivery rate, can be adjusted to hours, days, weeks, months, and even years by varying the preparations of the variously resorbing components.

A strongly resorbing calcium phosphate is characterized as follows: when at least 0.1 gram (preferably 0.1-0.5 g) is implanted in an osseous, subcutaneous or intramuscular site, at least 80% of the material is resorbed within one year. In more preferred embodiments, 0.5 gram of the calcium phosphate will be resorbed within nine months, six months, three months, and ideally one month or less, depending of the desired delivery profile desired at the tumor site. Weakly resorbable means that less than 80% of 0.1 gram of starting calcium phosphate is resorbed after one year. Resorption, as used herein, encompasses solubility based dissolution processes, as well as active cellular or enzyme based processes. Preferred materials are resorbed through active cellular or enzymatic processes. By controlling the rate of active degradation of the calcium phosphate cement, the inventive calcium phosphate cements can be tailored to have linear resorption rates, and can be tailored to avoid initial high concentration spikes where undesirable.

Resorbability of the calcium phosphate vehicles also may be varied through the adjustment of one or more physical parameters including vehicle size, vehicle particle size, porosity, density, and/or crystallinity. For example, monolithic devices, on the order of one gram will resorb more slowly than one gram of the same material when in particulate form. Two or more of these parameters will generally be adjusted in concert to fine-tune the final resorption rate.

For precipitated calcium phosphates, particle sizes may be controlled by careful control of the precipitation rate. Rapid precipitation, followed by rapid harvesting of the precipitate, is useful in the production of small particle sizes (e.g. particle size ranging from 5 nm to 150 nm) of low crystallinity. The use of standard milling processes known to the art (e.g. ball mills, roller mills, jet mills) followed by precise sieving, will also be useful in preparing vehicles of specific size particles. In other instances materials prepared from slurries, as described in the art, will produce useful particle size materials. Particle sizes of less than 1 mm, preferably less than 0.5 mm, are generally preferred for delivery vehicles intended to be resorbed within six months.

Cements can be induced to form particulates during hardening through the use of an emulsifying agent and injection of the cement as an emulsion. Emulsifying agents will be solubilized from the hardened material leaving a macropore matrix. Suitable emulsifying agents include lethicin, dimethicone, and the like.

Density of the hardened calcium phosphate composition also has a significant effect on resorption rates. Different calcium phosphate compositions result in different density and grain sizes. Higher density or larger grain size, of course, reduce resorption rates. Leachable or biodegradable materials may be incorporated into the paste that may be subsequently removed in vivo, e.g., by dissolution or cellular action, so that a porous vehicle results. Suitable additives should of course be biocompatible and physiologically acceptable at the doses required to induce porosity. Other methods of affecting calcium phosphate density are discussed in Driessens et al. in *Enclyclopedic Handbook of Biomaterials and Bioengineering*, Chapter 31, "Calcium Phosphate Bone Cements", Wise (Ed.), Marcel Dekker (1995).

Selection of the particular calcium phosphates may be made to provide a desired resorption rate in the device. Control of the calcium phosphate cement degree of crystallinity and crystal size may be used to affect the overall vehicle resorption rate. For apatitic calcium phosphates with calcium to phosphorous ratios of 1.3-1.75, poorly crystalline forms are believed to resorb more slowly than less crystalline forms, e.g., amorphous calcium phosphates. This may be an advantage in some applications where sustained release over long time periods is desired. For example, in a comparable in vivo site, calcium phosphate cements prepared with nanocrystalline calcium phosphate, and in particular with nanocrystalline calcium phosphate and dicalcium phosphate dihydrate, resorb slowly, e.g., over the course of more than one month. Increased resorption rates may be achieved through the production of apatitic calcium phosphates containing lattice defects, such as ionic vacancies or substitutions. Preferred embodiments include carbonated or otherwise calcium deficient apatites, i.e., Ca/P<1.67, all of which tend to have increased in vivo resorption rates. Each type of calcium phosphate cement may be preferred in specific therapeutic settings.

Further guidance for the production of similar such apatitic calcium phosphates can be found in *Structure and Chemistry of the Apatites and Other Calcium Orthophosphates*, (Elsevier, Amsterdam, 1994, by J. C. Elliott), and the references contained therein, all incorporated herein by reference.

The inventive delivery vehicle can be of any porosity that provides the desirable characteristics for anticancer drug delivery. Porosity facilitates both the diffusion of substances to and from the inventive material and, in certain applications, the penetration of cells and cell processes into the material matrix. Accordingly, calcium phosphate cements of lower porosity tend to resorb more is slowly in vivo than those of higher porosity; therefore, the greater the porosity, the greater the rate of resorption. In one embodiment of the invention, porosity is increased through the use of a dry mixture of controlled particle size reactants. For example, a reactant with a larger particle size (e.g. 300-500 μm) will produce a more porous material. Soluble porogens may also be used to control the porosity of the calcium phosphate material.

Additionally, certain molecular factors may be incorporated into the vehicle that can be used to affect its resorption rate by influencing the cellular or enzymatic processes that ordinarily mediate vehicle resorption in the body. These incorporated factors are often biologically active molecules or collections thereof, which affect bone metabolic processes, such as the activity of osteoclasts and/or osteoblasts. In other instances the incorporated factors attract or otherwise affect the activity of one or more of macrophages, monocytes, or foreign body giant cells. Such useful factors include: growth factors, enzyme inhibitors, extracellular matrix components, cytokines and the like.

Incorporation of factors, which attract or inhibit osteogenic cells and/or macrophages, can have a significant effect on calcium phosphate cement resorption rate. Thus, incorporation of bone morphogenetic protein into the inventive calcium phosphate cements will lead to more rapid resorption of the vehicle, particularly in soft tissue implant sites. Additionally, factors that attract osteoclasts (e.g. interleukin-1, lymphotoxin, calcitonin) may be used to promote degradation of the vehicle. Osteoclast or macrophage activity inhibitors (e.g. neutral phosphate, glucocorticoids, plicamycin, gallium nitrate) may be used to prolong the resorption process. Extracellular matrix components, such as laminen, RDG peptides, collagen, fibronectin may also be included with the calcium phosphate cements. Further guidance regarding specific factors useful in the regulation of calcium phosphate resorption rates can be found in PCT/US97/18528, incorporated by reference herein. Generally, these factors will be incorporated into the inventive calcium phosphate cements as a concentration of less than 20% wt/wt preferably less than 10% and in most embodiments, less than 5%.

In many instances, calcium phosphate cement resorbability is preferred; however, it is not always required or desired. In some embodiments, a calcium phosphate cement that is either weakly resorbable or substantially non-resorbable may be used. A non-resorbable calcium phosphate cement may be used when prolonged chemotherapy is required over a matter of several years. A non-resorbable calcium phosphate cement may also be desirable in cases when the calcium phosphate cement is used additionally as a support matrix for tissue repair or growth, as a treatment for a disease. Non-resorbable calcium phosphate calcium phosphate cements can remain in the body without detrimental effects to the host due to their excellent biocompatibility. Alternatively, non-resorbable calcium phosphate cements may be surgically removed following the desired delivery period. Suitable non-resorbable or weakly resorbable calcium phosphate calcium phosphate cements include those prepared from sintered hydroxyapatite.

Ultimately, resorption rates may be established empirically by using intramuscular or subcutaneous implantation of the calcium phosphate cement in one or more small animal models to assess the exact effect of formulation adjustments on calcium phosphate cement resorption rates. In these model systems, a variety of candidate formulations may be tested simultaneously and resorption rates can be compared at various time points using standard histological, radiographic or other methods know to the art.

The calcium phosphate paste may also be formulated in a manner which enhances its receptiveness to the cancer cells. For example, the pH of the delivery vehicle may be tailored to be particularly receptive to cancer cells. Cancer cells typically produce an environment that is of lower pH (more acidic) than that associated with healthy host cells. The composition of the calcium phosphate paste may be selected to provide a resultant hardened calcium phosphate having a pH which enhances the effectiveness of the anticancer therapy. Practitioners of calcium phosphate chemistry will know to use those calcium phosphates having the least solubility (for longer release times) at the expected pH at physiological temperatures. In most embodiments, the composition is selected for pH stability at neutrality or under slightly acidic conditions. Guidance for preparations of calcium phosphate cements of differing pHs can be found in the solubility isotherm data such as that provided by Brown in "Phase relationships in the ternary system $CaO-P_2O_5-H_2O$ at 25 C," Amer. Ceram. Soc. 75:17(1992) and by J. C. Elliot in "*Structure and Chemistry of the Apatites and Other Calcium Orthophosphates*," supra.

The invention also provides a method for the treatment of cancer. The method includes administering an anticancer composition to a tumor site of a patient. The anticancer composition includes a mixture of an anticancer agent in a calcium phosphate paste delivery vehicle. The paste is made up of two or more calcium phosphates and a physiologically acceptable fluid, each calcium phosphate having a Ca/P ratio of less than or equal to 1.7. The paste is injectable or formable at the time of administration which allows the paste to be introduced directly at and into the tumor. The paste then hardens rapidly at the tumor site.

The method of the invention has been investigated for the treatment of breast and prostate cancer, although the methods and compositions described herein may be readily adapted for the treatment of many kinds of cancer.

EXAMPLE 1

This example illustrates the typical formation of a nanocrystalline calcium phosphate (NCP) gel for use in a drug delivery preparation for delivery of a chemotherapeutic.

A solution of 218 g of disodium $Na_2HPO_4.12\ H_2O$ in 1.2 liters of distilled water and a solution of 70 g of $Ca(NO_3)_2.4H_2O$ in 0.5 liters of distilled water were prepared. The calcium solution was quickly poured into the phosphate solution at room temperature with stirring. Precipitation was immediate and substantially complete. The precipitate was adjusted to pH 6.4 by the addition of sodium hydroxide solution in order to avoid the formation of acidic calcium phosphates. The precipitate was aged at room temperature for 5 minutes prior to filtration. The precipitate was then filtered through a Buchner filter (with a total surface about 0.1 m$^2$), and was washed by about 3 liters of distilled water. A gel cake of nanocrystalline calcium phosphate obtained on the filter paper.

EXAMPLE 2

This example illustrates the typical formation of a nanocrystalline calcium phosphate (NCP) powder for use in a drug delivery preparation for delivery of a chemotherapeutic.

The calcium phosphate apatite material was prepared according to example 3 but with the following modifications. The washed precipitate was collected using a spatula and immersed into liquid nitrogen in a 2.5 L container. Following freezing, the container was transferred into a vacuum chamber for 24 hours ($10^{-1}$-$10^{-2}$ torr), until a fine and dry powder was obtained.

EXAMPLE 3

This example illustrates the preparation of an apatitic calcium phosphate drug delivery agent for delivery of a chemotherapeutic using NCP powder.

NCP was made by combining two solutions at room temperature. Solution A contained 87.6 g calcium nitrate tetrahydrate in 624 mL of distilled water (pH 5.45). Solution B contained 203.7 g dibasic sodium phosphate heptahydrate and 100.0 g sodium bicarbonate in 2000 mL of distilled water. After mixing together for two minutes at room temperature (pH 6.60), 42 mL of 10% wt/wt NaOH solution was added to the reaction mixture over 11 minutes to bring the pH to 7.29. The mixture was filtered by vacuum filtration (650 mL per funnel) and washed four times with 1000 mL of distilled water. After the last wash, the material was covered in liquid nitrogen and lyophilized for 24 hours. After lyophilization, the powder was pushed through a 500 μm sieve.

Dicalcium phosphate dihydrate (DCPD) was prepared at room temperature by the rapid addition of solution B (17.1 g $Ca(NO_3)_2.4H_2O$; 0.250 liters distilled water; pH 5.5-60 to a stirred solution A (10 g $H_9N_2O_4P$; 0.5 liters distilled water; pH 7.8). Immediately thereafter, the sample was filtered using filter paper (0.05 sq. m) with medium filter speed and a vacuum pressure of about $10^{-2}$ torr. The material formed a thin cake which was washed with about 2 liters of distilled water and then dried at room temperature for 24-72 hours.

The nanocrystalline calcium phosphate material was physically dry-mixed with DCPD at 50:50 weight percent using a mortar and pestle for 3-5 minutes. Water (1 ml/g of mixed material) was then added to the powder mixture to yield a hydrated precursor of paste-like consistency. The amount of $H_2O$ added varied, depending on whether a thick or thin paste was desired. The paste material was then placed in a moist tissue environment where upon reaching body temperature (37° C.), it hardened into a solid mass. The hardening process could be delayed for several hours by placing it into a refrigerating temperature of 4° C.

EXAMPLE 4

The goal of this study was to use a calcium phosphate material as a delivery vehicle for cisplatin at a mammary tumor site and to evaluate the effectiveness of cisplatin-calcium phosphate delivery system in treating MTGB Mouse cancer tumors in C3H mice.

A protocol was established to administer a two component calcium phosphate delivery vehicle using the material of Example 6 to a tumor interior. The material was tested at two different cisplatin dosage levels and compared against a systemically delivered control. Table 4 includes the protocol used for the mice study (total of 80 athymic nude mice).

TABLE 4

Group 1: Positive control (Dose 1-25 mg/kg IV systemic control); n = 12
Group 2: Positive control (Dose 2-10 mg/kg IV systemic control); n = 12
Group 3: Negative control (no treatment); n = 11
Group 4: Dose 1-25 mg/kg 50:50 NCP/DCPD inside tumor; n = 11
Group 5: Dose 2-10 mg/kg 50:50 NCP/DCPD inside tumor; n = 11
Group 6: Negative control (50:50 NCP/DCPD only inside tumor); n = 12

The mice were C3H mice (approx. 20 g). They were housed in solid bottom mouse cages maintained within a semi-rigid isolator. They were fed an 18% protein, 5% fat rodent laboratory chow fed ad-lib, gamma-irradiated prior to use. Water was sterile filtered and provided in water bottles. Ambient temperature is 72 degrees F.±5 degrees with a relative humidity of 50%±20%.

Mice were innoculated subcutaneously in the flank area with $1\times10^6$ tumor cell in 0.1 mL of RPMI culture medium. After tumors had grown to 8-10 mm, 0.1 cc of treatment or control materials (except for positive systemic controls which were administered by IV) were injected directly into the tumor with an 18-gauge needle. The positive control cisplatin solution was prepared by dissolving a specified amount of cisplatin in sterile saline for injection through a 25 gauge needle directly into the tumor. The appropriate calcium phosphate delivery vehicle was supplied as a sterile powder in a preweighed package. At the time of injection, each powder was hydrated with the appropriate amount of saline and loaded into a 0.1 cc syringe for injection through a 16 gauge needle. Each material was mixed on site and immediately injected at the tumor site using a 1 cc syringe with a Luer-Lok® tip and a 16-gauge needle. At the study site, each animal was weighed and its tumor size was recorded, using hand-held calipers for the measurements. Mice were sacrificed when tumor mass was greater than 10% of body weight.

Animals were monitored over a 20-day period for changes in body weight and tumor mass. Tumor shrinkage accompanied by the absence of toxic side effects (as determined by loss of body weight) was considered an indication of successful treatment.

Figure 2:
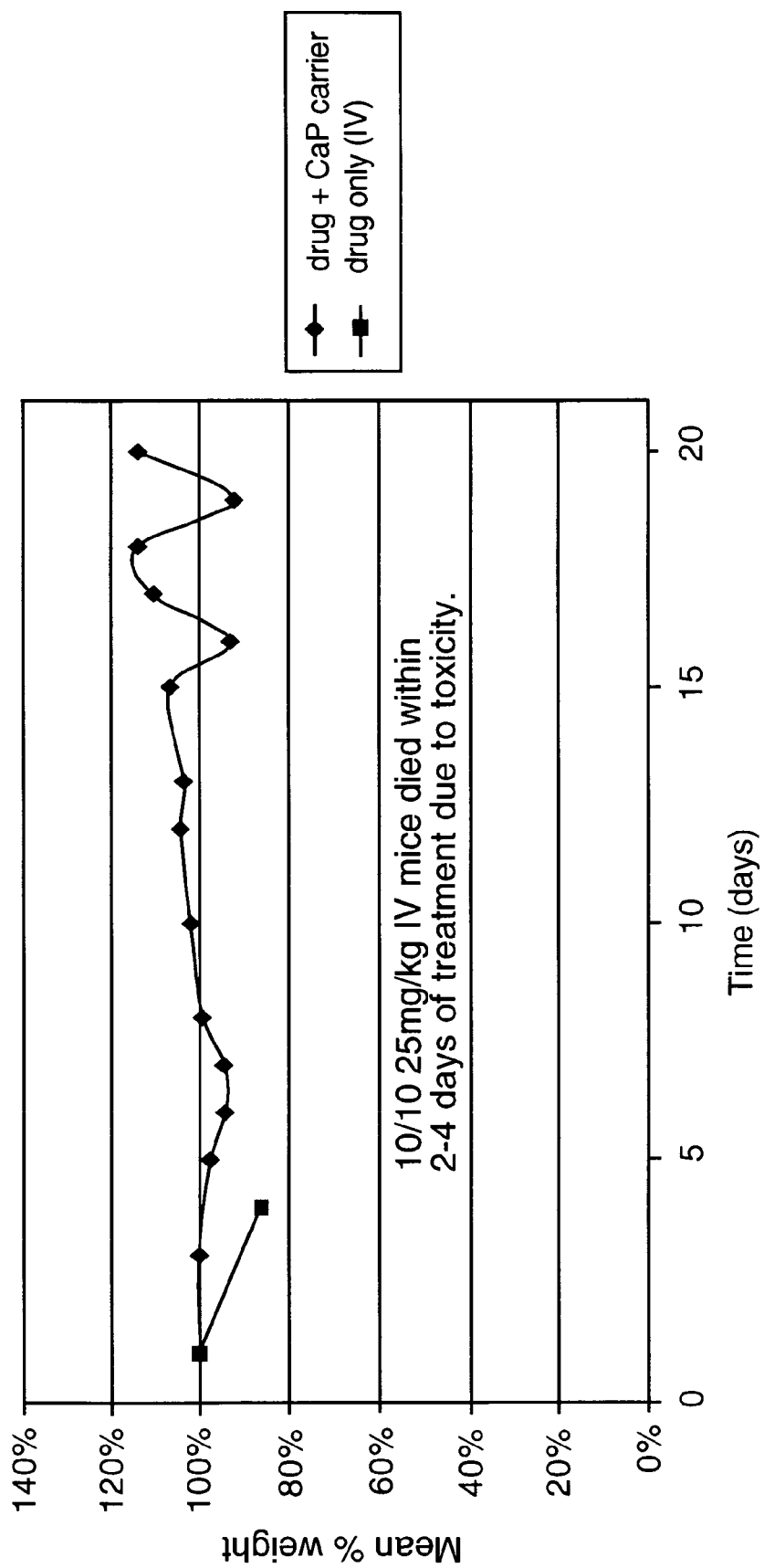
FIG. 2 is a plot of total body weight over time for C3H mice treated with cisplatin in calcium phosphate delivery vehicle of the invention (♦), and for rats treated with a positive control (intravenous administration) (■)

FIG. 1 is a plot of the % tumor mass change over time for 25 mg/kg cisplatin dose in calcium phosphate delivery vehicle (▲), calcium phosphate delivery vehicle alone (*), no treatment (+), and systemic IV administration of 25 mg/kg cisplatin (−). As is clearly shown, negative control animals (curves (*) and (+)), which received no chemotherapy, demonstrated rapid and excessive tumor is growth. The animals were sacrificed on Day 7 due to excessive tumor load. The plot clearly demonstrates that the cisplatin locally delivered to the tumor in a calcium phosphate delivery vehicle based on NCP/DCPD matched the ability of intravenous delivery of cisplatin (positive control); however, positive control animals died on Day 5 due to excessive weight loss. See, FIG. 2. Positive control animals, however, remained active and apparently healthy over the 20 day observation period.

EXAMPLE 5

The goal of this study was to use a calcium phosphate material as a delivery vehicle for cisplatin at a prostate cancer tumor site and to evaluate the effectiveness of cisplatin-calcium phosphate delivery system in treating DU-145 human cancer tumors in nude mice.

A protocol was established to administer a two component calcium phosphate delivery vehicle using the material of Example 6 to a tumor interior. The material was tested at two different cisplatin dosage levels and compared against a systemically delivered control. Table 5 includes the protocol used for the mice study (total of 36 NU/NU-nuBR nude mice).

TABLE 5

Group 1: Positive control (Dose 1-25 mg/kg IV systemic control); n = 6
Group 2: Positive control (Dose 2-10 mg/kg IV systemic control); n = 6
Group 3: Negative control (no treatment); n = 6
Group 4: Dose 1-25 mg/kg 50:50 NCP/DCPD inside tumor; n = 6
Group 5: Dose 2-10 mg/kg 50:50 NCP/DCPD inside tumor; n = 6
Group 6: Negative control (50:50 NCP/DCPD only, inside tumor); n = 6

The mice were female 5-6 week old Crl:NU/NU-nuBR, which are nude outbred mice. mice (approx. 17-21 g). They were housed in solid bottom mouse cages maintained within a semi-rigid isolator. They were fed a 18% protein, 5% fat rodent laboratory chow fed ad-lib, gamma-irradiated prior to use. Water was sterile filtered and provided in water bottles. Ambient temperature is 72 degrees F.±5 degrees with a relative humidity of 50%±20%.

Mice were inoculated subcutaneously in the flank area with $2\times10^6$ tumor cell in 0.1 mL of RPMI culture medium with 30% Matrigel. After tumors had grown to 100±35 mg, 0.1 cc of treatment or control materials (except for positive systemic controls which were administered by IV) were injected directly into the tumor with an 18-gauge needle. The positive control cisplatin solution was prepared by dissolving a specified amount of cisplatin in sterile saline for injection through a 25 gauge needle directly into the tumor. The appropriate calcium phosphate delivery vehicle was supplied as a sterile powder in a preweighed package. At the time of injection, each powder was hydrated with the appropriate amount of saline and loaded into a 0.1 cc syringe for injection through a 16 gauge needle. Each material was mixed on site and immediately injected at the tumor site using a 1 cc syringe with a Luer-Lok® tip and a 16-gauge needle. At the study site, each animal was weighed and its tumor size was recorded, using hand-held calipers for the measurements. Mice were sacrificed when two consecutive tumor mass measurements greater than 1000 mg were recorded.

Animals were monitored over a 20-plus day period for changes in body weight and tumor mass. Tumor shrinkage accompanied by the absence of toxic side effects (as determined by loss of body weight) was considered an indication of successful treatment.

Figure 3:
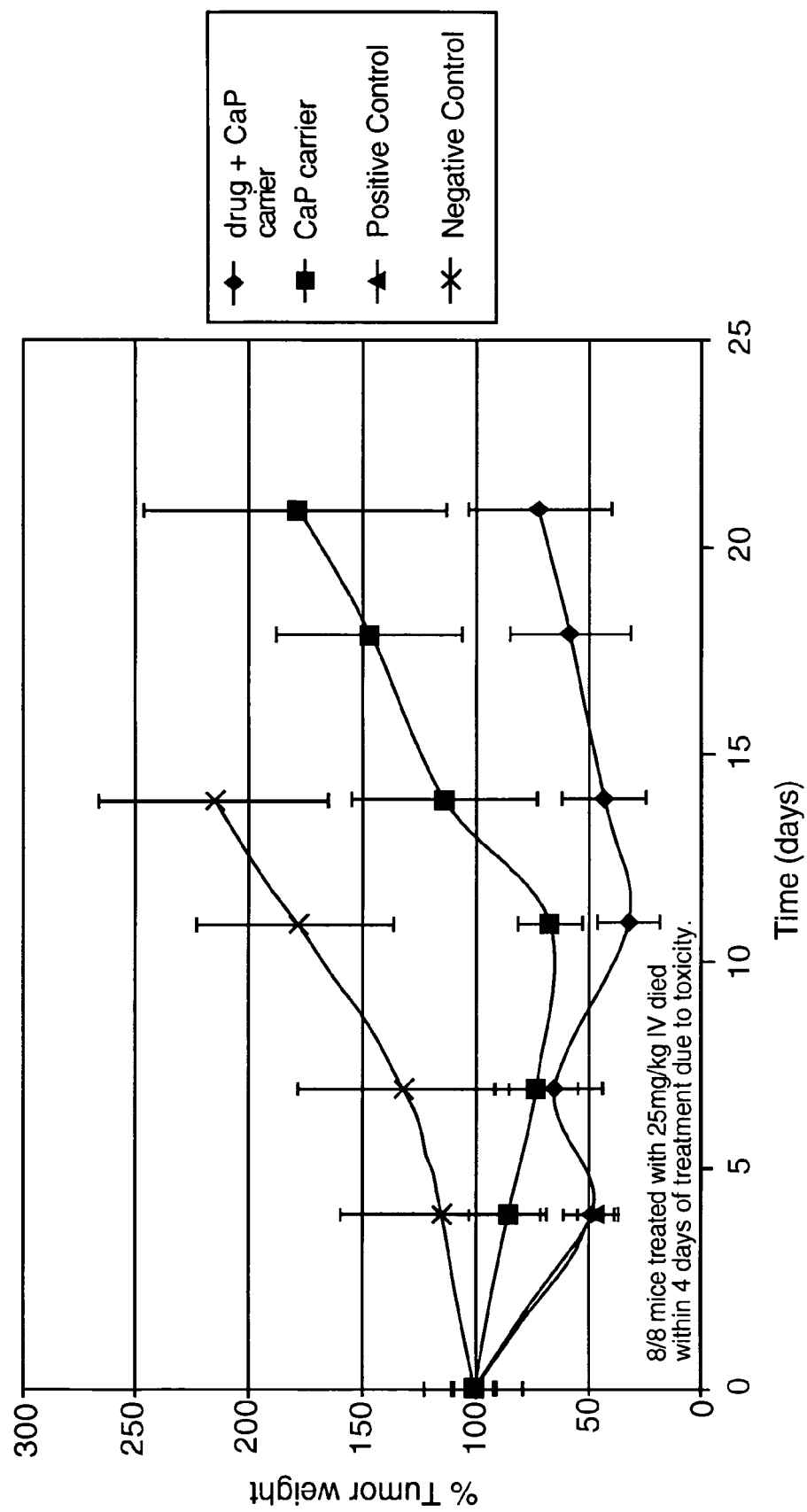
FIG. 3 is a plot of the % tumor mass change over time for C3H mice for 25 mg/kg cisplatin dose in calcium phosphate delivery vehicle (▲), calcium phosphate delivery vehicle alone (*), no treatment (+), and systemic IV administration of cisplatin (−)
Figure 4:
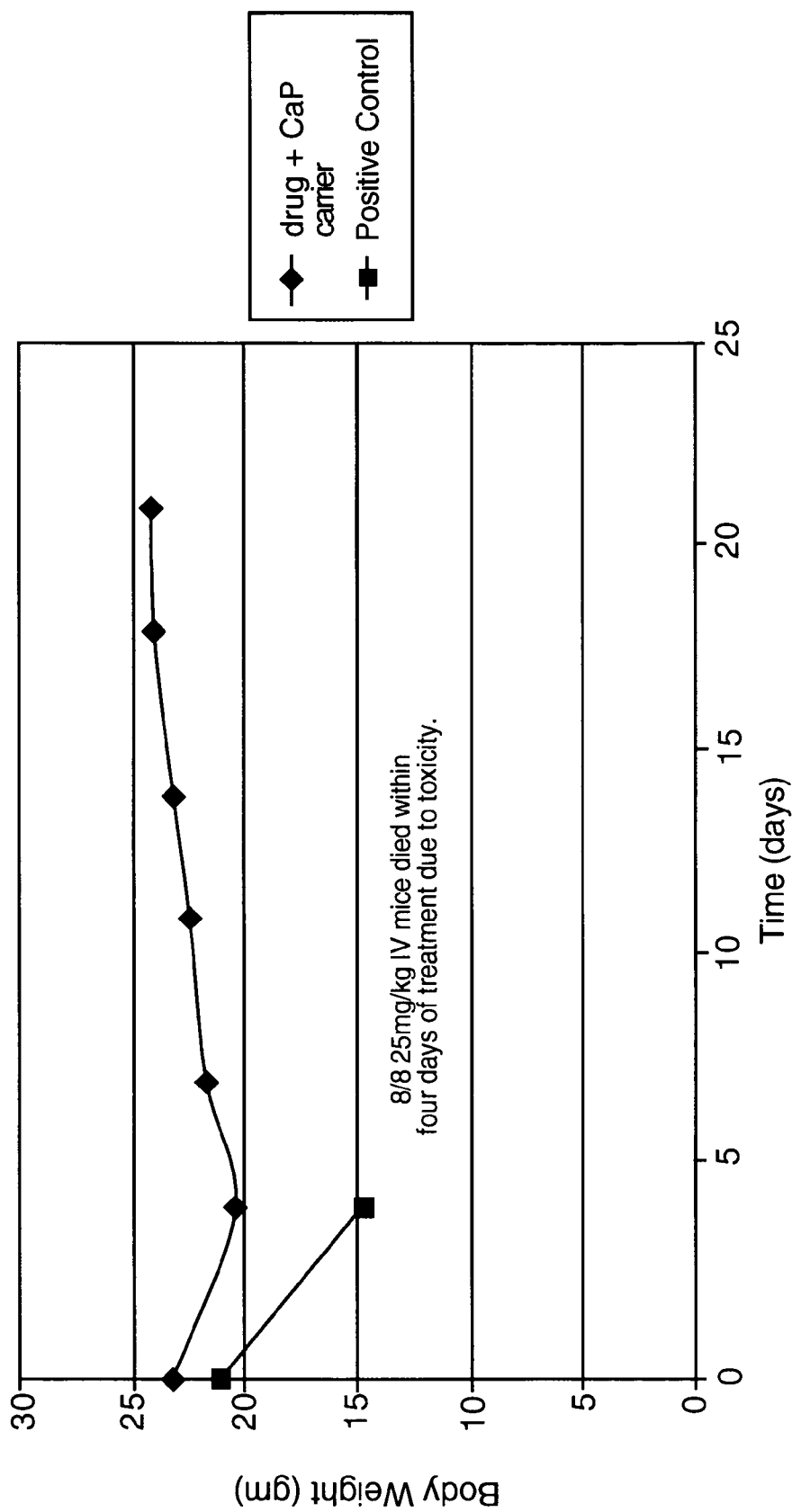
FIG. 4 is a plot of total body weight over time for C3H mice treated with cisplatin in calcium phosphate delivery vehicle of the invention (♦), and for rats treated with a positive control (intravenous administration) (■).

FIG. 3 is a plot of the % tumor mass change over time for (a) 25 is mg/kg cisplatin dose in calcium phosphate delivery vehicle, (b) calcium phosphate delivery vehicle alone, (c) no treatment and (d) systemic IV administration of 25 mg/kg cisplatin. As is clearly shown, negative control animals (curve (b)), which received no chemotherapy, demonstrated rapid and excessive tumor growth. The animals were sacrificed on Day 14 due to excessive tumor load. The plot clearly demonstrates that the cisplatin locally delivered to the tumor in a calcium phosphate delivery vehicle based on NCP/DCPD matched the ability of intravenous delivery of cisplatin (positive control) to contain tumor growth; however, positive control animals died on Day 4 due to excessive weight loss. See, FIG. 4. Positive control animals, however, remained active and apparently healthy over the 21 day observation period.

What is claimed is:

1. An anticancer composition comprising:
    (i) a calcium phosphate comprising an amorphous calcium phosphate (ACP) or a poorly crystalline apatitic (PCA) calcium phosphate;
    (ii) an anticancer agent; and
    (iii) a physiologically acceptable fluid,
    wherein said composition is formulated as a formable or injectable paste that hardens in an endothermic reaction.

2. The composition of claim 1, wherein said ACP or PCA calcium phosphate has a Ca/P ratio of less than or equal to 1.5.

3. The composition of claim 1, wherein said anticancer agent is selected from the group consisting of methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomustine, dacarbazine (DTIC, dimethyltriazenomideazolecarboxamide), 5-fluorouracil, cytarabine, cytosine arabinoside, 6-mercaptopurine, tamoxifen, flutamide, thioguanine, and mixtures thereof.

4. The composition of claim 1, wherein the anticancer composition is formulated for administration by cannula or by injection.

5. The composition of claim 1, wherein said composition further comprises one or more calcium phosphates selected from the group consisting of dicalcium phosphate dihydrate (DCPD), tricalcium phosphate (TCP), heptacalcium phosphate, calcium pyrophosphate, calcium metaphosphate, octacalcium phosphate (OCP), and hydroxyapatite (HA).

6. The composition of claim 1, wherein said ACP or PCA calcium phosphate has a calcium to phosphate ratio in the range of 1.2 to 1.68.

7. The composition of claim 1, wherein said composition is injectable or formable for longer than ten minutes.

8. The composition of claim 7, wherein said composition is injectable or formable for longer than one hour.

9. A method for treating cancer in a mammal, said method comprising administering the composition of claim 1 to said mammal.

10. The method of claim 9, wherein said mammal is a human.

11. The composition of claim 1, wherein said composition comprises DCPD and ACP.

12. The composition of claim 1, wherein said composition comprises DCPD and PCA calcium phosphate.

* * * * *